United States Patent [19]

Kesling

[11] Patent Number: 5,415,542
[45] Date of Patent: May 16, 1995

[54] ORTHODONTIC FINISHING APPLIANCE

[75] Inventor: Peter C. Kesling, LaPorte, Ind.

[73] Assignee: TP Orthodontics, Inc., Westville, Ind.

[21] Appl. No.: 203,815

[22] Filed: Mar. 1, 1994

[51] Int. Cl.$^6$ ............................................. A61C 3/00
[52] U.S. Cl. ........................................................ 433/6
[58] Field of Search ..................... 433/6; 128/861, 862

[56] References Cited

U.S. PATENT DOCUMENTS

| | | | |
|---|---|---|---|
| 3,178,820 | 4/1965 | Kesling | 433/6 |
| 3,837,081 | 9/1974 | Kesling | 433/6 |
| 4,371,336 | 2/1983 | Hilleman | 433/6 |
| 5,028,231 | 7/1991 | Hall | 433/6 |
| 5,145,364 | 9/1992 | Martz et al. | 433/6 |
| 5,163,839 | 11/1992 | Metcalf | 433/6 |
| 5,173,048 | 12/1992 | Summer | 433/6 |
| 5,203,695 | 4/1993 | Bergerson | 433/6 |

OTHER PUBLICATIONS

TO Orthodontics, Inc. catalog, 1992, p. 190.
Sergl, Hans Georg, "Concept And Use Of The Idealistator," Prakt Kieferorthop 2, 1988, pp. 11–18.
Sergl, H.-G., "The Idealisator-A Functional End Device Of Permanently Soft Plastic," Fortschr. Kieferorthop. 50 (Nr. 4), 1989, pp. 338–346.

Primary Examiner—Cary E. O'Connor
Attorney, Agent, or Firm—Lloyd L. Zickert

[57] ABSTRACT

An orthodontic appliance used to finalize or perfect the relationships between the teeth of a patient following the removal of fixed appliances or, in minor cases, instead of fixed appliances, which includes a resilient body having ideally related sockets to accept portions of the upper and lower teeth, a wire anchored in the body of the appliance arranged to engage the labial and/or buccal surfaces of some or all of the upper teeth, and embrasure engaging devices to enhance proper placement and retention of the appliance.

36 Claims, 2 Drawing Sheets

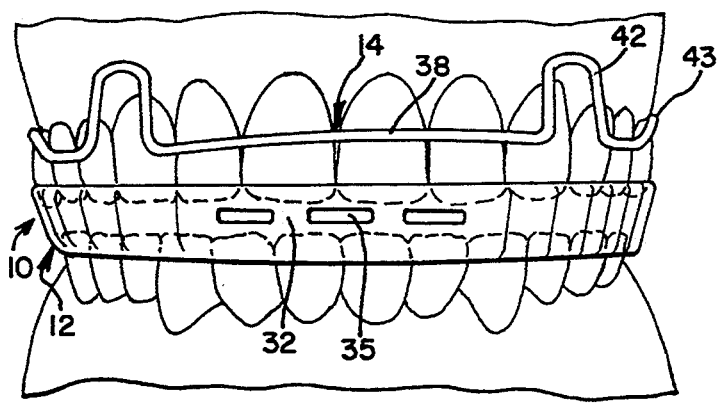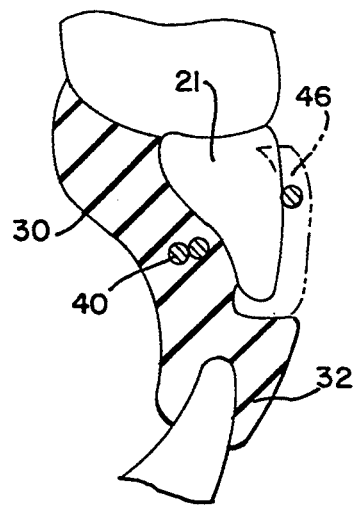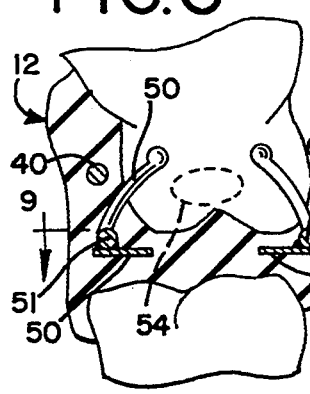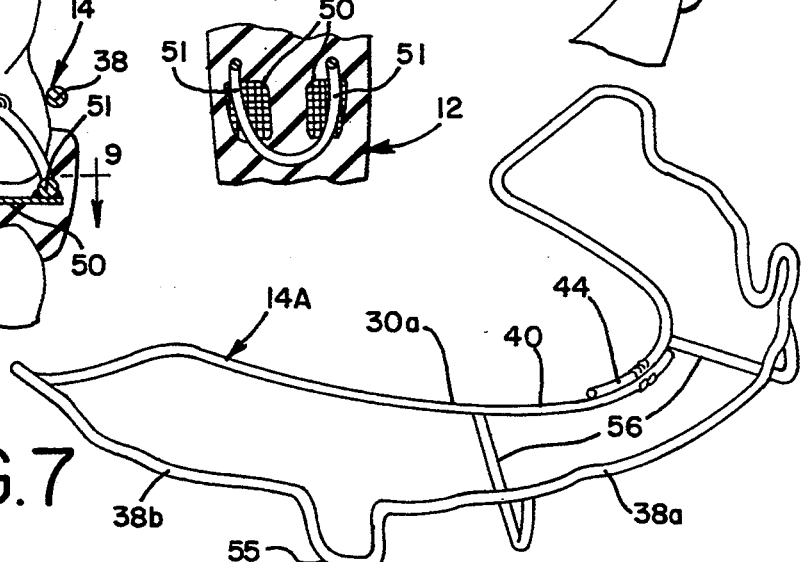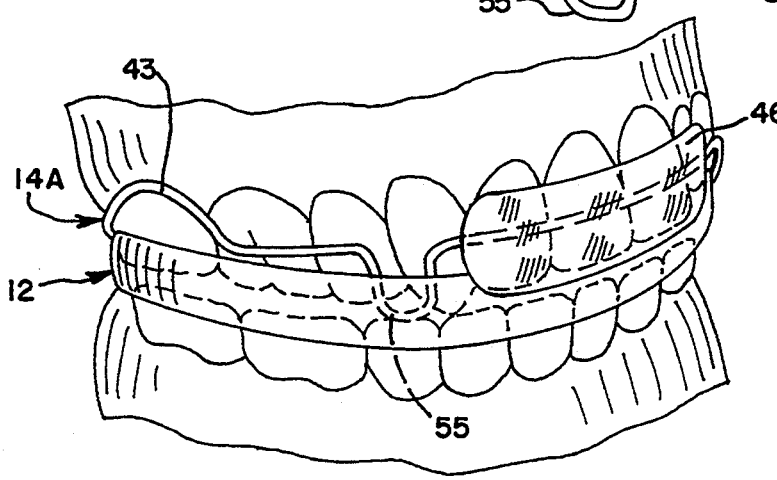

ORTHODONTIC FINISHING APPLIANCE

DESCRIPTION

This invention relates in general to an improved appliance for finishing orthodontic treatment that is both aesthetic and comfortable, and more particularly to an appliance that simplifies placement and enhances retention.

BACKGROUND OF THE INVENTION

Heretofore, it has been known to provide a tooth positioning appliance of resilient material for use following the removal of fixed appliances to bring the teeth into ideal occlusion, as disclosed in U.S. Pat. No. 2,531,222. Tooth positioning appliances, commonly called tooth positioners, are very demanding on patients as they are bulky, uncomfortable and prevent patients from speaking.

It also has been well known to utilize removable retainers made of a rigid acrylic and flexible wires for purposes of retaining and slightly changing the positions of teeth following treatment with fixed appliances. Retainers are much easier to wear than tooth positioners, are more aesthetic and permit the patient to open and close his/her mouth for speaking. However, the degree and type of tooth movements possible from retainers are limited by their rigid bodies and the skill of the orthodontist when making sequential adjustments at periodic visits by the patient.

Further, it has been known to reduce tooth positioners in size by reducing the gingival contacting portions, such as done by the Position-ette appliance made by TP Orthodontics, Inc. of Westville, Ind., to make them more acceptable, but such positioners may still not be readily accepted by patients for the reasons mentioned above. Position-ette is a registered trademark owned by TP Orthodontics, Inc. It also has been well known to provide both custom and preformed tooth positioners with clasps to enhance placement and retention as disclosed in U.S. Pat. Nos. 3,178,820 and 3,837,081.

Moreover, an appliance has been known which reduces in size the mass bulk of positioners and includes a retaining wire for the anterior teeth. However, this appliance is not self-retaining and lacks adequate control of the teeth, especially the upper posterior teeth, and therefore is recommended for the correction of a few selected teeth only, while the others remain unmoved to aid in retention of the appliance.

SUMMARY OF THE INVENTION

The heretofore known problems of finishing orthodontic treatment have been solved by the finishing appliance of the present invention with the attributes of a tooth positioning appliance as well as a retainer to provide the ultimate in occlusal perfection without placing undue demands on the manual skills of the orthodontist or the ability of the patient.

The appliance of the present invention includes a body of soft resilient material which includes impressions or sockets to accept portions of the upper and lower teeth, and a control or retention wire anchored in the body of the appliance for engaging some or all of the labial and/or buccal surfaces of the upper teeth. The appliance may either be custom made by being formed over a setup of the patient's own teeth or preformed in various sizes with the proper size selection being made by measuring the patient's teeth.

The appliance also includes one or more rigid plates preferably made of clear rigid plastic attached to the wire to engage selected buccal and/or labial surfaces of the upper teeth for increased retention and to provide more positive corrective pressures and final control of these teeth, and/or clasping devices anchored in the body of the appliance.

Accordingly, it is an object of the present invention to provide a new and improved self-retaining finishing appliance for orthodontic treatment of a patient which combines the functions of a tooth positioning appliance and a retainer.

It is a further object of the present invention to provide a new and improved self-retaining finishing appliance for orthodontic treatment of a patient which combines the functions of a tooth positioning appliance and a retainer, and includes at least one gingival embrasure engaging device, such as a clasp or a plate, to enhance proper placement and retention of the appliance.

Another object of the present invention is in the provision of an orthodontic finishing appliance capable of combining tooth-positioning and retainer functions and which includes a resilient body with impressions formed over a setup of the patient's teeth and having a clasping device for enhancing placement and retention and a control or retainer wire for engagement with some or all of the labial and/or buccal surfaces of the upper teeth.

Another object of the invention is to provide a preformed "off-the-shelf" orthodontic appliance that is readily acceptable and easily worn by the patient which includes a resilient body, ideally related sockets or impressions to accept at least portions of the crowns of the upper and lower teeth, interproximal clasping devices to aid in the proper seating and retention of the appliance, and a control wire to engage some or all of the buccal and/or labial surfaces of the upper teeth.

A still further object of the present invention is to provide an orthodontic finishing appliance having a resilient body with ideally located sockets for receiving the crowns of the teeth, embrasure clasping devices to enhance seating and retention, a control wire to engage upper teeth, and one or more teeth engaging pads on the wire to further enhance control.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 4 is a front view of the appliance of FIG. 1 illustrating the manner in which the teeth are associated with the appliance;

FIG. 5 is a detailed sectional view taken substantially along the line 5—5 of FIG. 3, and also showing a rigid anterior plate in phantom as illustrated in the embodiment of FIG. 8;

FIG. 6 is a detailed sectional view taken substantially along the line 6—6 of FIG. 3, and also showing wire mesh anchors attached to the retention clasp for increasing clasp anchorage;

FIG. 7 is a three-quarter perspective view of the control or retainer wire prior to being molded into the resilient body of the appliance and modified over the embodiment of FIGS. 1 to 4 to have the adjusting loops extending downwardly and partially embedded in the body;

FIG. 8 is a three-quarter perspective view of another embodiment of the appliance in place between the upper and lower dental arches including the wire version of FIG. 7 and an optional rigid plate mounted to the labial portion of wire; and FIG. 9 is a detailed sectional view taken substantially along line 9—9 of FIG. 6 to show the wire mesh anchor in plan view.

DESCRIPTION OF THE INVENTION

The orthodontic appliance of the invention is a removable appliance that is prescribed for a patient to finish treatment following the removal of fixed appliances, and particularly to perfect, idealize, and finalize the relationships between adjacent teeth on the upper and lower arches and the relationship of the teeth of one arch to the teeth of the other arch. The appliance of the invention may be custom made for a particular patient, or it may be preformed in accordance with average statistically sized arches.

When the appliance is custom made, it is made from a setup, as disclosed in U.S. Pat. No. 2,775,036, which generally consists of making an impression of the patient's teeth, constructing a model of the teeth from the impression, and rearranging one or more of the teeth on the model to their ideal or desired locations.

When the appliance of the invention is preformed, so that it can be fitted to a patient immediately after removal of fixed appliances, it is made in accordance with average anatomical dimensions. Further, such a preformed appliance can be provided for several classes and in various sizes to fit different arches and teeth to produce the best possible fit. For example, TP Orthodontics, Inc. sells preformed tooth positioners for different classes of cases, such as non-extraction and extraction cases, and in various sizes ranging from 40 to 60 mm.

The appliance of the invention may also be made with air holes or airways such as disclosed in U.S. Pat. No. 4,195,046 to facilitate breathing.

Figure 1:
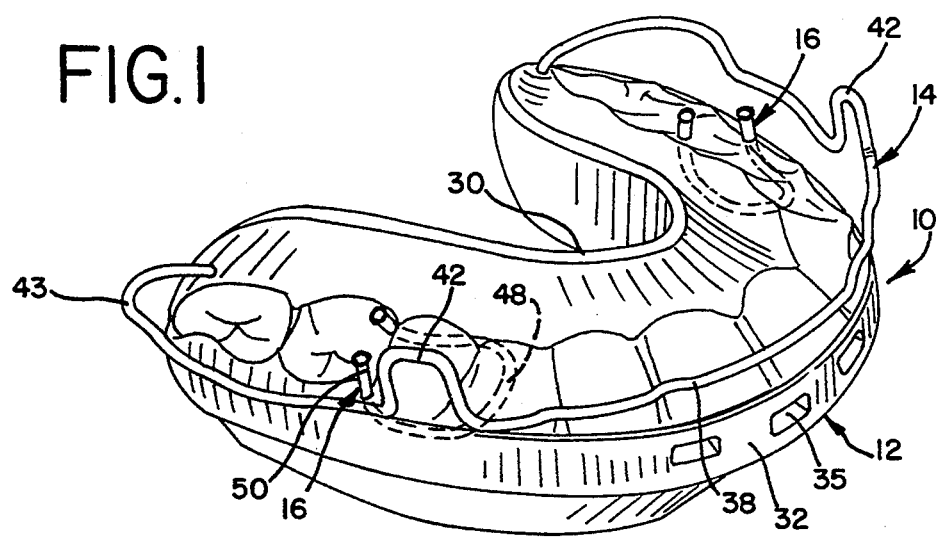
FIG. 1 is a three-quarter perspective view of one embodiment of the finishing appliance of the present invention.
Figure 2:
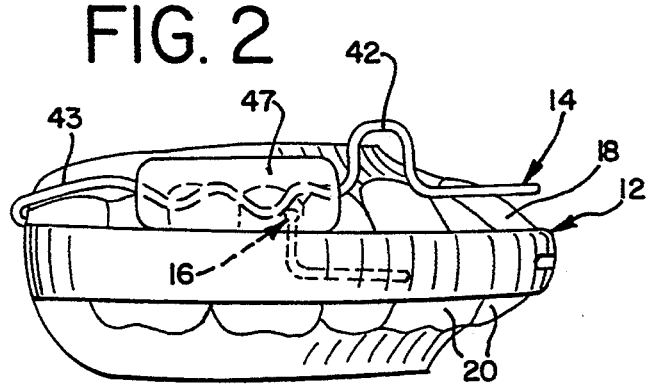
FIG. 2 is a side elevational view of the finishing appliance of FIG. 1, and also showing an optional hard plastic pad or plate mounted on a buccal portion of the control wire.
Figure 3:
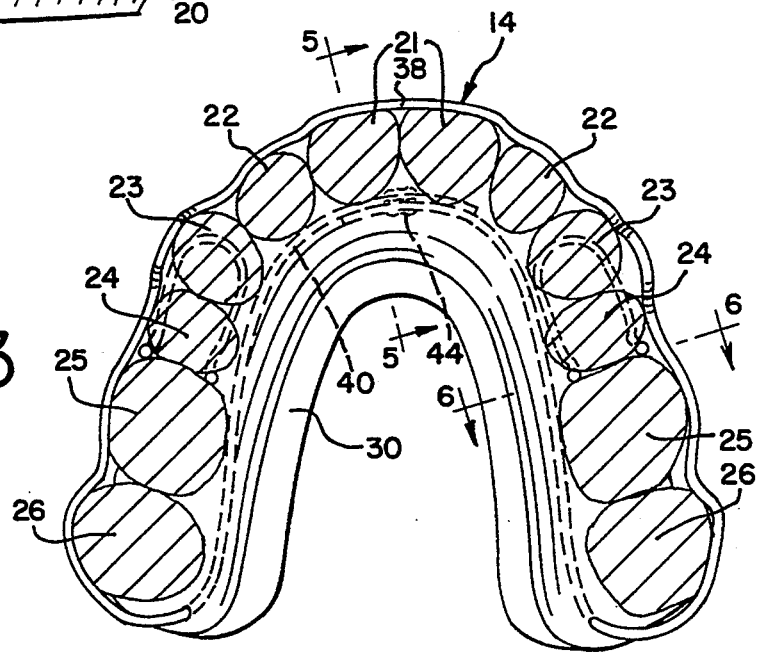
FIG. 3 is a top plan view of the appliance of FIG. 1 illustrating the outlines of the upper tooth crowns in their sockets/impressions and the wire touching their buccal and labial surfaces.

The orthodontic appliance of the invention generally includes a body of resilient material having upper and lower tooth impressions or sockets which are generally sized to cover the incisal and occlusal portions of the crowns, all or a portion of the lingual surfaces of the upper and lower tooth crowns, and also a small part of the labial/buccal surfaces of the crowns. One or more horizontal control wires are carried by the resilient body for engaging part or all of the labial and/or buccal surfaces of the upper teeth. Optionally, one or more rigid acrylic pads or plates are formed on the wire or wires to increase surface contact and control of the upper teeth, and/or to enhance placement and retention. Thus, the plates may be formed to further enhance the placement and retention of the appliance as clasping devices to engage in the gingival embrasure areas between some of the teeth. The clasping devices also may be in the form of clasps, as illustrated in FIGS. 1 to 3. The form of one or more rigid plates having gingival embrasure-engaging projections is illustrated in FIGS. 2, 5 and 8. It should also be appreciated that both clasping devices may be employed in an appliance.

The resilient body is made from a suitable material such as rubber or any number of plastic resins to produce the desired resilience and wear characteristics, while the wire and clasps are made of a suitable stainless steel. More particularly, the body may be made of Odontosil silicone, available from Dreve-Dentamid-GmbH of Unna, Germany. This material, when processed, has a durometer hardness of about 55 Shore A.

Referring now to the drawings, and particularly to FIGS. 1 to 4, the removable appliance of the invention is generally indicated by the numeral 10 and includes a resilient body 12, a wire 14 for engaging the labial and buccal surfaces of the upper teeth, and a pair of clasps or seating springs 16, one at each side of the upper arch.

The resilient body 12 is made of a suitable resilient material such as a rubber compound or a plastic resin compound and, as previously mentioned, may be custom made over a setup of the teeth of a patient or preformed of a suitable size to be immediately placed with the patient. The body is arch-shaped and includes a plurality of sockets or teeth impressions 18 in the upper arch and a plurality of sockets or teeth impressions 20 in the lower arch.

It may be appreciated that the number of sockets or teeth impressions may vary from appliance to appliance depending upon the patient for which it is to be used. Similarly, preformed appliances may be provided with any desired number of sockets. The illustrated embodiment is made for a patient having centrals 21, laterals 22, cuspids 23, bicuspids 24, first molars 25, and second molars 26. The area of the mouth adjacent the centrals, laterals and cuspids may be considered the labial or anterior area, while the area adjacent the bicuspids and molars may be considered the buccal or posterior area. Accordingly, the sockets or teeth impressions are arranged for receiving these teeth and particularly the crowns of the teeth.

The body 12 also includes an arch-shaped lingual section 30 within which the tongue may be disposed during wearing of the appliance, and a labial-buccal ridge or flange portion 32 sized to generally cover at least part of the incisal and occlusal portions of the crowns. In any event, the height of the flange 32 normally would not be such as to engage upper or lower gums or gingiva, while the lingual portion 30 generally would be formed such as to substantially cover the lingual surfaces of the upper and lower teeth and a portion of the gums. As seen particularly in FIG. 4, the upper and lower sockets are vertically spaced apart to define a freeway space so as to enhance the comfort of the wearer when the teeth are bottomed in the sockets. Also, the area between the upper and lower sockets, which constitutes the freeway space, may include airways or air holes 35 which extend between the labial and lingual surfaces of the body, as shown in FIG. 4. These air holes are provided in the appliance to facilitate breathing. Then holes may be molded, drilled or otherwise formed and take any suitable cross-sectional shape.

The control wire 14 is formed and mounted on the body 12 to engage the labial and buccal surfaces of the upper teeth. The wire includes a labial/buccal section 38 formed to engage the labial and buccal surfaces of the upper teeth and an anchoring portion 40 embedded in the body of the appliance. The wire is continuous and may include one or more adjusting loops 42 to facilitate adjustment as needed to assure desired contact with the labial and buccal surfaces of the teeth. Preferably, these loops are mesial to the bicuspids. The part of the wire engaging the anterior teeth may be strictly arcuate or formed to the shape of the outer teeth, as seen more particularly in Fig. 3. Further, the distal portions of the labial/buccal section 38 preferably follow the gum line at 43 to provide the best possible fit on the upper arch. Thus, the wire 14 engages over the buccal/labial surfaces of the upper teeth from the anterior teeth to the posterior teeth and then the wire enters the body of the appliance behind and somewhat lingual to the rearmost molar, as illustrated in FIG. 1, so that the anchoring portion 40 will be embedded in the body lingual to the upper teeth.

The wire is made from a suitable length of stainless steel wire and bent into the desired form, and the ends are suitably secured together, such as by spot-welding, as indicated at 44 in FIGS. 3 and 7. It will be appreciated that the positions of the adjusting loops 42 are preferably between the anterior teeth which constitute the front six teeth of each arch and the posterior teeth which constitute the rear six teeth of each arch.

While the control wire 14, as illustrated, is formed to contact the labial and buccal surfaces of all of the upper teeth, it will be appreciated that the wire may be formed to contact only a portion of the upper teeth. For example, it may be desirable that the wire not contact the bicuspids, and in that event an anterior wire would be formed to contact the centrals, laterals and cuspids, and posterior wires could be formed to contact the first and second molars. However, it would be preferable that the wire at least in part contact the labial and buccal surfaces of all upper teeth.

Where it might be desired to provide additional control over the teeth, one or more acrylic pads or plates may be molded onto the control wire 14 to provide contact with a greater area of the teeth. Thus, such a pad or plate is connected to the body through the control wire. As seen in FIGS. 5 and 8, a single acrylic pad or shield 46 is molded onto the anterior portion of the wire 38 to contact the four upper incisors and perhaps a portion of the canines. Further, as seen in FIG. 2, an acrylic pad 47 can be molded to a posterior portion of the control wire to provide additional control over those teeth. It will be understood that the acrylic pad 46 and/or 47 is a rigid or hard material, and further that the lingual side of the pad may be smooth or custom formed to mate with the teeth and include projections extending into the gingival embrasure areas between the teeth to enhance placement and retention. The labial/buccal side is smooth so as to minimize irritation of the tissues.

The plate or pad may be of any suitable height and width to cover a small or large portion of the labial/buccal surfaces of the teeth. Preferably, the plate will overlap at least two adjacent teeth and be molded to the shape of the surfaces with projections to engage in the gingival embrasures to enhance retention of the appliance, as shown in FIG. 5. The plate formed for the anterior teeth may merely cover a small portion of the labial surfaces, or substantially all of the labial surfaces of the centrals and laterals as well as the incisal or occlusal edges as illustrated most clearly in FIGS. 5 and 8. Further, where the plate is formed to engage over the incisal surfaces, the resilient body 12 is formed to accommodate the plate. The portion of the wire on which the plate is molded may be relatively straight, as shown in FIG. 8 for the plate 46, or undulated, as shown in FIG. 2 for the plate 47.

The clasps 16 engage in gingival embrasure areas of the teeth to enhance placement and retention and are anchored in the body of the appliance. These clasps are preferably made from a spring steel so that they have the flexibility to expand around the contact areas between teeth and properly coact with the embrasure areas between teeth during placement and removal. Each of the clasps 16 includes an anchoring portion 48 in the form of a loop which is embedded in the resilient body as particularly seen in FIGS. 1 to 3. The clasps include arms 50 extending into the interproximal areas between the bicuspids 24 and the first molars 25 and in converging relation so as to engage in the gingival embrasure areas. Further, the arms may include balled ends 52 to avoid any sharp edges that could damage tissues and facilitate their slipping around the contact points. The embrasure areas between the adjacent teeth are defined as the areas around the contact area 54 of the teeth, as illustrated in FIG. 6. Thus, one of the arms will come in from the buccal side and the other from the lingual side to engage in the gingival embrasure areas to grip the teeth. The balled ends will snap over the contact area and thereby enhance the proper placement of the appliance on the teeth as well as the retention of the appliance on the teeth. While only a pair of clasps is illustrated, it may be appreciated that any number of clasps may be included and they may be provided in both the upper and the lower arches. Further, in order to enhance the anchoring of the clasps in the resilient body 12, wire mesh pads 50 can be suitably welded or soldered to the anchoring legs 51 of the clasps.

The embodiment of FIGS. 7 and 8 differ from the embodiment of FIGS. 1 to 4 in that the rigid anterior plate 46 is molded on the control wire 14A as above noted, and adjusting loops 55 are provided and directed occlusally with their tips molded into the resilient body 12. By directing the adjusting loops 55 occlusally, the control wire is additionally anchored to the appliance body, thereby providing a firmer interaction between the body and the wire, while still permitting adjustability of the wire.

Further, cross-anchoring members 56 may extend from the lingual anchoring section 30a to the labial section 38a. These cross members 56 are optional and when included serve to additionally anchor the wire to the body and also to reinforce the overall integrity of the wire and rigidify the relative positions of the labial/buccal sections 38a and/or 38b. In FIG. 7, the anchoring cross members 56 are disposed mesial to the anchoring loops 55 although they may be disposed distal to the loops if desired. It will be appreciated the cross members 56 are optional and if included may be disposed along the wire at any suitable location and in any suitable number.

In view of the foregoing, it will be appreciated that the appliance of the invention solves the problem of bulk and aesthetics by substantially reducing the height of the sockets on the labial and buccal sides, provides the desired control of the upper teeth with the use of one or more wires which contact the labial and buccal surfaces of the upper teeth, and enhances placement and retention by providing means for extending into gingival embrasure areas. Thus, the appliance provides an efficient removable finishing appliance to be used following fixed appliance treatment. The appliance may include the clasps 16 having projections engaging the gingival embrasure areas between teeth for the purpose of enhancing placement and retention, or one or more rigid plates on the wire which have projections extending into gingival embrasure areas between teeth and otherwise formed to mate with the teeth, or both clasps and/or one or more rigid plates. It will be appreciated the plates also provide better control of those teeth they engage.

It will be understood that modifications and variations may be effected without departing from the scope of the novel concepts of the present invention, but it is understood that this application is to be limited only by the scope of the appended claims.

The invention is hereby claimed as follows:

1. A custom-made orthodontic finishing appliance made over a setup of a patient comprising:
   a body of resilient material having impressions of at least some of the occlusal and/or incisal portions of the crowns of the upper and lower teeth arranged for obtaining ideal occlusion of the teeth,
   a control wire anchored in the body for engaging the labial and/or buccal surfaces of the upper teeth,
   and means engaging gingival embrasure areas between teeth for enhancing proper placement and retention of the appliance.

2. The appliance of claim 1, wherein the wire includes at least one adjusting loop for permitting the fit of the wire to the teeth to be adjusted.

3. The appliance of claim 2, wherein the adjusting loop extends gingivally.

4. The appliance of claim 2, wherein the adjusting loop extends occlusally and is embedded in the body.

5. The appliance of claim 4, wherein the resilient material is silicone.

6. The appliance of claim 1, wherein the wire includes a plurality of adjusting loops.

7. The appliance of claim 6, wherein the adjusting loops extend gingivally.

8. The appliance of claim 6, wherein the adjusting loops extend occlusally and are partially embedded in the body.

9. The appliance of claim 8, wherein the adjusting loops are mesial to the bicuspids.

10. The appliance of claim 8, wherein the impressions further include surfaces matching a very small part of the labial and/or buccal surfaces of the teeth near the incisal and occlusal.

11. The appliance of claim 1, wherein the means enhancing placement and retention includes means extending into at least one gingival embrasure.

12. The appliance of claim 1, wherein the means enhancing placement and retention includes clasps anchored in the body having projections going into buccal and lingual gingival embrasure areas.

13. The appliance of claim 1, wherein the means enhancing placement and retention includes at least one rigid plate mounted on the control wire and having one or more projections extending into one or more gingival embrasure areas.

14. The appliance of claim 1, wherein the body of resilient material is relatively soft.

15. The appliance of claim 1, wherein the body of resilient material has a durometer hardness in the range of 55 Shore A.

16. The appliance of claim 1, wherein the body is U-shaped and the impressions include surfaces matching the incisal and occlusal surfaces of the teeth.

17. The appliance of claim 1, wherein the resilient body is made of soft plastic material.

18. The appliance of claim 1, wherein the control wire includes an anchoring section embedded in the body and disposed lingually of the teeth impressions.

19. The appliance of claim 1, wherein the control wire includes an anchoring section embedded in the body, and at least one cross member is connected between the control wire and the anchoring section, said cross member being anchored in the body between the upper and lower teeth impressions.

20. The appliance of claim 1, which further includes at least one substantially rigid plate on the control wire adapted to contact the labial and/or buccal surfaces of a plurality of teeth.

21. The appliance of claim 20, wherein the plate is adapted to contact only the labial surfaces of a plurality of teeth.

22. The appliance of claim 20, wherein the plate is formed to contact one or more labial gingival embrasure areas between a plurality of teeth.

23. The appliance of claim 20, wherein the plate is formed to contact the buccal gingival embrasure areas between a plurality of teeth.

24. The appliance of claim 20, wherein the plate is formed to contact labial surfaces of a plurality of teeth and have at least one projection engaging an embrasure area between two adjacent teeth.

25. The appliance of claim 20, wherein the plate is adapted to contact only the buccal surfaces of a plurality of teeth.

26. The appliance of claim 20, wherein a rigid plate is molded on the control wire for engaging the anterior teeth.

27. The appliance of claim 20, wherein the rigid plate includes a portion formed over the incisal edges of the teeth.

28. The appliance of claim 20, wherein the body further includes air holes to allow the wearer to breath through the mouth when the appliance is worn.

29. The appliance of claim 20, wherein a rigid plate is molded on the control wire for engaging posterior teeth.

30. A preformed orthodontic finishing appliance comprising:
   a body of resilient material having impressions of at least some of the incisal and occlusal portions of the crowns of the upper and lower teeth arranged for obtaining ideal occlusion of the teeth,
   means for engaging gingival embrasure areas between teeth to enhance proper placement and retention of the appliance,
   and a control wire anchored in the body for engaging the labial and/or buccal surfaces of the upper teeth.

31. The appliance of claim 30, wherein a rigid plate is molded on the control wire for engaging the anterior teeth.

32. The appliance of claim 30, wherein a rigid plate is molded on the control wire for engaging posterior teeth.

33. The appliance of claim 30, wherein the control wire includes at least one adjusting loop.

34. The appliance of claim 33, wherein the adjusting loop extends gingivally.

35. The appliance of claim 33, wherein the adjusting loop extends occlusally and is anchored in the body.

36. The appliance of claim 35, wherein the adjusting loop is mesial to the bicuspid.

* * * * *